(12) United States Patent
Harms

(10) Patent No.: US 7,828,231 B2
(45) Date of Patent: Nov. 9, 2010

(54) DISCHARGE HEAD FOR FLUIDS

(75) Inventor: Heiko Harms, Menden (DE)

(73) Assignee: MeadWestvaco Calmar GmbH, Hemer (DE)

( * ) Notice: Subject to any disclaimer, the term of this patent is extended or adjusted under 35 U.S.C. 154(b) by 387 days.

(21) Appl. No.: 11/995,790

(22) PCT Filed: Jul. 7, 2006

(86) PCT No.: PCT/EP2006/006663

§ 371 (c)(1),
(2), (4) Date: Jan. 15, 2008

(87) PCT Pub. No.: WO2007/009617

PCT Pub. Date: Jan. 25, 2007

(65) Prior Publication Data

US 2008/0230633 A1    Sep. 25, 2008

(30) Foreign Application Priority Data

Jul. 15, 2005    (DE)  ................. 10 2005 033 771

(51) Int. Cl.
*B05B 1/30* (2006.01)
(52) U.S. Cl. .................. 239/533.1; 239/333; 239/451; 239/456; 239/468; 239/487; 239/490; 239/491; 239/533.15; 239/601; 222/321.6; 222/340

(58) Field of Classification Search ................ 239/333, 239/451, 456, 459, 468, 469, 482, 487, 490, 239/491, 533.1, 533.15, 569, 583, 601; 222/321.6, 222/321.7, 340, 420, 422; 128/200.14
See application file for complete search history.

(56) References Cited

U.S. PATENT DOCUMENTS

| | | | | | |
|---|---|---|---|---|---|
| 4,124,163 | A | * | 11/1978 | Siegmann | ............... 239/533.15 |
| 5,203,840 | A | * | 4/1993 | Graf et al. | ................. 222/321.6 |
| 6,095,376 | A | * | 8/2000 | Hennemann et al. | ...... 222/321.6 |
| 6,189,739 | B1 | * | 2/2001 | von Schuckmann | ......... 222/340 |
| 6,308,867 | B1 | * | 10/2001 | Wolter | ...................... 222/321.6 |
| 7,182,226 | B2 | * | 2/2007 | Mbonyumuhire | ........... 239/333 |

* cited by examiner

*Primary Examiner*—Steven J Ganey
(74) *Attorney, Agent, or Firm*—MWV Intellectual Property Group

(57) ABSTRACT

A discharge head for fluids, with a discharge nozzle (1) which has a discharge opening (2) and accommodates an internal sleeve (5) in which is arranged an internal body (4) which delimits an outlet channel (7) and has a connecting element (8) for connection to a counterpart (9) of a discharging apparatus, the internal sleeve (5) having, on the end side adjacent to the discharge opening (2), a sealing surface (10) against which a valve stopper (3) which is located on the internal body (4) and closes the outlet channel (7) is spring prestressed.

33 Claims, 1 Drawing Sheet

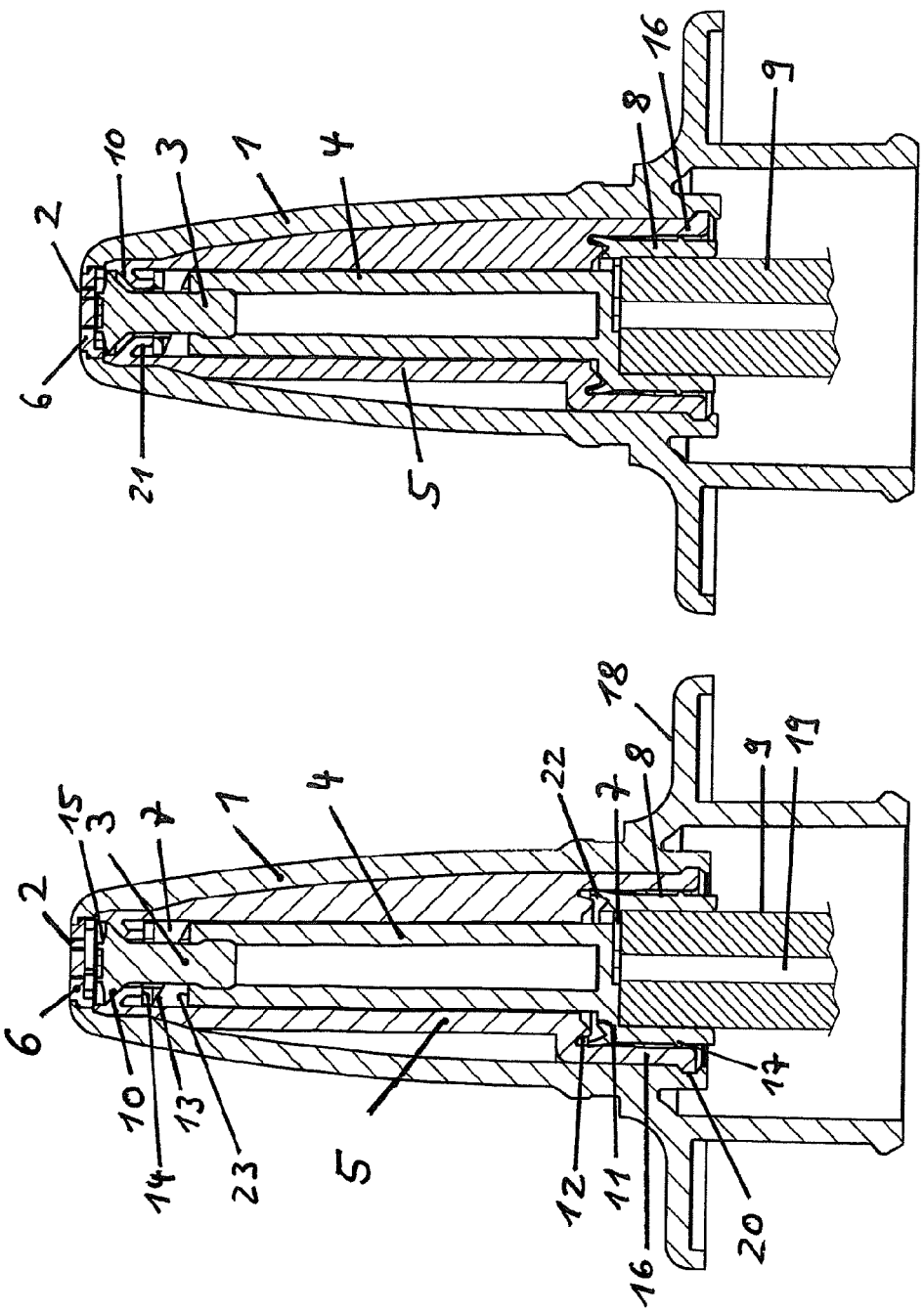

DISCHARGE HEAD FOR FLUIDS

CROSS-REFERENCE TO RELATED APPLICATIONS

This application claims priority to and the benefit of PCT Application No. PCT/EP2006/006663, entitled "FLUIDAUSTRAGKOPF," filed 7 Jul. 2006, which claims priority from German Application 10 2005 033 771.6 DE, entitled "FLUIDAUSTAGKOPF," filed 15 Jul. 2005, and incorporates each of the same herein by reference in their entireties.

BACKGROUND OF THE INVENTION

1. Field of the Invention

The invention relates to a discharge head for fluids and more particularly to discharge heads for pharmaceutical formulations.

2. State of the Art

Discharge heads for fluids, for use with a discharging apparatus, are known in diverse forms from the prior art.

EP 0 443 192 A2 discloses a discharge head for media, which comprises a discharge nozzle which has a discharge opening and is designed with an internal sleeve. The internal sleeve accommodates, approximately over the entire length, the stem of an internal body that produces a direct connection to a counterpart of a discharging apparatus. The entire actuating pressure is thus essentially transmitted to the counterpart via the internal body and dead spaces are reduced. It is disadvantageous that germs and other impurities can penetrate the system through the discharge opening.

DE 198 40 723 A1 discloses a discharge head for media, which has a discharge nozzle, the dispensing outlet of which can be closed in a microbiologically sealed manner by a valve stopper which can be closed counter to the direction of flow. Before a pump stroke, the valve is opened against a spring counter to the direction of flow. In this case, the closing gap of the valve forms the media outlet. The medium can be protected as a result against germ contamination. It is disadvantageous that a discharge head of this type with its closure directly at the discharge opening impairs the spray mechanism. In addition, the valve obstructs the handling.

It is therefore desirous to provide a discharge head for fluids, which may ensure easy handling and which may reduce the risk of contamination of the medium.

BRIEF SUMMARY OF THE INVENTION

According to certain embodiments of the invention a discharge head for fluids may have a discharge nozzle which has a discharge opening and accommodates an internal sleeve in which an internal body may be arranged which arrangement delimits an outlet channel. The internal body may have a connecting element for connection to a counterpart of a discharging apparatus such as a pump, wherein the internal sleeve may include a sealing surface against which a valve stopper located in the internal body may rest or contact to close the outlet channel. The valve stopper may be spring prestressed or stressed to ensure closure between the sealing surface and the valve stopper.

According to other embodiments of the invention, a fluid dispenser may include a discharge nozzle with a discharge opening in which a nozzle insert is positioned. An internal sleeve may be positioned in the discharge nozzle and may have a sealing surface adjacent to the discharge opening. The internal sleeve may also include an inner bush, a spring seat, and attachment element, and a snap connection, wherein the snap connection may hold the internal sleeve within the discharge nozzle. An internal body may be positioned in the internal sleeve and may be held in that position by a connecting element in communication with the attachment element. The communication between the connection element and the attachment element may allow axial movement of the internal sleeve with respect to the internal body. A valve stopper may be positioned in the internal body or may be integral to the internal body. The valve stopper may rest on the sealing surface of the internal sleeve, closing an outlet channel formed between the internal sleeve and the internal body. A compression spring or other spring mechanism may be arranged between the internal body and the internal sleeve adjacent to the valve stopper opening. Movement of the internal sleeve with respect to the internal body may open the outlet channel. Fluid from a reservoir may be pumped or transported to the outlet channel through a pump or other fluid discharge apparatus.

BRIEF DESCRIPTION OF THE DRAWINGS

The invention is explained in more detail below with reference to the exemplary embodiments illustrated in the attached figures, in which FIG. 1 illustrates an axial section of a discharge head for fluids in a basic position, unactuated; and FIG. 2 illustrates in axial section, the discharge head for fluids according to FIG. 1 in a position with the valve open for a subsequent discharging operation.

DETAILED DESCRIPTION OF THE INVENTION

According to embodiments of the invention, a discharge head is provided, in which a valve is integrated in the discharge nozzle. A dead volume between the discharge opening and the valve is kept small. The valve-guiding movement in the axial direction is designed as compulsory movement. Before any medium at all is conveyed, the valve is therefore opened compulsorily by the actuating force applied by the user.

The valve here can be formed on an internal sleeve which, by being supported on a connecting element of the internal body, reliably and directly transmits the actuating forces which occur, with a stroke for the opening of the valve being oriented via guides.

The valve can be of small dimensions, and therefore oligodynamic substances which can additionally be used do not make the production of the discharge head substantially more expensive. Should there not be sufficient sterilization, the valve can therefore optimally be set by embedded, oligodynamic substances into the position to effectively protect against bacteria and germs.

The spring for the spring prestressing can be formed by an end of the internal body such that the internal sleeve can be supported on the end side directly on the internal body. The actuating forces then likewise act directly on the internal body which transmits the actuating forces to the counterpart as a function of the spring travel. The actuating forces for opening the valve and for transmitting to the counterpart act on the same internal body.

The valve stopper is preferably designed as a functional element for forming a jet at the outlet opening. For this purpose, the valve stopper may be designed as a swirling body. As an alternative, the valve stopper may be designed so as to restrict swirling devices in the head region of the discharge nozzle. For this purpose, the valve stopper may have an end cone.

Embodiments of the invention relate to a discharge head for fluids, for use with a discharging apparatus (not illustrated specifically), the discharging apparatus comprising a medium reservoir for a fluid, in which the medium is placed under pressure or from which the medium is discharged via a medium pump, in particular a sliding piston pump. The discharging apparatus has a counterpart 9 to which the discharge head for fluids can be attached.

The discharge head for fluids comprises a discharge nozzle 1 with a discharge opening 2 which is fitted here on the end side of the discharge nozzle 1. The discharge nozzle 1 accommodates an internal sleeve 5 in which is arranged an internal body 4 which delimits an outlet channel 7 and has a connecting element 8 for connection to the counterpart 9 of a discharging apparatus. The internal sleeve 5 has, on the end side adjacent to the discharge opening 2, a sealing surface 10 against which a valve stopper 3 rests. The valve stopper 3 is located on the internal body 4 and closes the outlet channel 7 and is spring prestressed.

The discharge nozzle 1 has finger supporting surfaces 18 for manual actuation with actuating forces being applied to the counterpart 9. The discharge nozzle 1, which serves to pass on the fluid discharged from the media container, is connected, by means of its outlet channel 7, to a passage channel 19 of the counterpart 9. The discharge nozzle 1 is in the form of an olive-shaped nose in order to be able to be placed onto the counterpart 9 as a nose adaptor. For other application purposes, the discharge nozzle 1 may have different external contours.

At the end region, the discharge nozzle 1 has, on the end side, the discharge opening 2 which may comprise one or more openings depending on the spray or jet pattern desired.

The internal sleeve 5 sits in a fixedly arranged manner in the discharge nozzle 1, with the fastening to the discharge nozzle 1 taking place releasably via a snap connection 20. The internal sleeve 5 is inserted in the region of its end which bears the sealing surface 10 into the discharge nozzle 1 in a flush manner, as a result of which the sealing surface 10 obtains a stable position. On the rear side of the sealing surface 10, the internal sleeve 5 has a spring seat 14 for the spring prestressing of the valve stopper 3. The spring seat 14 is formed on an inner bush 21 which is formed integrally with the internal sleeve 5 and delimits the outlet channel 7 in relation to the valve stopper 3 as far as the sealing surface 10. The bush 21 is preferably arranged standing freely.

At the end facing the counterpart 9, the internal sleeve 5 has an attachment element 16 via which the internal sleeve 5 is fastened releasably to the discharge nozzle. Said attachment element 16 is pulled with axial play over the connecting element 8 of the internal body 4. This axial play permits an axial stroke of the discharge nozzle 1 together with the internal sleeve 5 in relation to the internal body 4 in order to raise the valve stopper 3 from the sealing surface 10, as illustrated in FIG. 2, before the counterpart 9 is actuated to dispense medium. The connecting element 8 forms a stop 11 for the internal sleeve 5. In order to improve the engagement of the internal sleeve 5 on the connecting element 8 for the transmission of the actuating forces, said internal sleeve bears protruding guide elements 12 which engage in depressions 22 matching them in shape on the stop 11 of the connecting element 8.

The internal sleeve 5 sits in a slidable manner on the internal body 4 which sits on the counterpart 9. The internal body 4 delimits the outlet channel 7 either with respect to the internal sleeve 5 or by means of an inner outlet channel and serves to minimize dead spaces in the discharge nozzle 1. In order to reduce weight, the internal body 4 may be of hollow design. For an at least partial radial minimum spacing of the attachment element 16 of the internal sleeve 5, the connecting element 8 has a radially projecting guide web device 17.

The valve stopper 3 is arranged on the internal body 4 on the head side, here, for example, by means of a snap connection. Accordingly, the valve stopper 3 is connected fixedly to the internal body 4. For the spring prestressing of the valve stopper 3 in relation to the sealing surface 10, a compression spring 13 is arranged between the rear side of the sealing surface 10 and an end side 23 of the internal body 4. The compression spring 13 is preferably formed integrally with the internal body 4, for which purpose the latter can bear an annular disk section on the end side. The spring seat 14 on the rear side of the sealing surface 10 is preferably formed on the bush 21. Alternative forms of compression springs can be used.

On the head side, the valve stopper 3 is expanded conically in order to form a funnel-shaped sealing surface 10 adjacent to the discharge opening 2. Furthermore, the valve stopper 3 preferably forms a swirling body with swirling devices 15 on the end side which, when the valve is open, as illustrated in FIG. 2, form a nozzle insert 6 together with the end of the discharge nozzle 1. As an alternative, the swirling devices may be formed on the end of the discharge nozzle 1 and the end side of the valve stopper may form a base surface for the nozzle insert formed in this manner.

Having thus described certain particular embodiments of the invention, it is understood that the invention defined by the appended claims is not to be limited by particular details set forth in the above description, as many apparent variations thereof are contemplated. Rather, the invention is limited only be the appended claims, which include within their scope all equivalent devices or methods which operate according to the principles of the invention as described.

The invention claimed is:

1. A discharge head for fluids comprising:
a discharge nozzle having a discharge opening;
an internal sleeve in the discharge nozzle and adjacent to the discharge opening;
a sealing surface on the internal sleeve;
an internal body on an interior of the internal sleeve and which delimits an outlet channel;
a valve stopper located on the internal body and in contact with the sealing surface to close the outlet channel, wherein the valve stopper is spring prestressed; and
a stop on the internal body, wherein the internal sleeve is moveable in relation to the internal body as far as the stop on the internal body.

2. The discharge head for fluids of claim 1, wherein the valve stopper comprises a moveable valve stopper that may be moved from contact with the sealing surface.

3. The discharge head for fluids of claim 1, wherein movement of the internal sleeve in relation to the internal body transmits an actuating pressure on the counterpart via the internal body.

4. The discharge head for fluids of claim 1, wherein the internal sleeve further comprises protruding guide elements.

5. The discharge head for fluids of claim 4, further comprising a stop on the internal body wherein the protruding guide elements may be brought into engagement with the stop.

6. The discharge head for fluids of claim 1, further comprising a compression spring.

7. The discharge head for fluids of claim 6, wherein the compression spring is supported between the internal sleeve and the internal body.

8. The discharge head for fluids of claim 6, wherein the compression spring comprises an annular disk formed integrally with the internal body.

9. The discharge head for fluids of claim 1, wherein the internal sleeve further comprises a spring seat.

10. The discharge head for fluids of claim 9, wherein the spring seat is positioned on the rear side of the sealing surface.

11. The discharge head for fluids of claim 1, wherein the valve stopper further comprises a valve stopper which when raised from the sealing surface forms a swirling device together with the discharge opening.

12. The discharge head for fluids of claim 11, wherein the valve stopper further comprises swirling devices located proximate the discharge opening.

13. The discharge head for fluids of claim 1, further comprising a nozzle insert positioned in the discharge opening.

14. The discharge head for fluids of claim 1, further comprising an attachment element on the internal sleeve wherein the attachment element may be pulled over the connecting element to lock the internal sleeve to the discharge nozzle.

15. The discharge head for fluids of claim 14, further comprising a guide web device in communication with the connecting element to produce at least a partial radial minimum spacing of the attachment element to the connecting element.

16. The discharge head for fluids of claim 1, further comprising:
a reservoir for a fluid; and
a pump for transporting fluid from the reservoir to the discharge head.

17. A discharge head, comprising:
a discharge nozzle;
a discharge opening in an end of the discharge nozzle;
an internal sleeve positioned within the discharge nozzle, comprising:
an attachment element;
an internal body positioned within the internal sleeve, comprising:
a connecting element, wherein the connecting element and the attachment element are in communication and allow limited axial movement of the internal sleeve with respect to the internal body;
an outlet channel;
a valve stopper; and
a spring mechanism positioned between the internal sleeve and the internal body.

18. The discharge head of claim 17, further comprising a nozzle insert positioned in the discharge opening.

19. The discharge head of claim 18, wherein the nozzle insert and the valve stopper define spin mechanics for a fluid discharge from the discharge head.

20. The discharge head of claim 17, wherein the internal sleeve further comprises a sealing surface in communication with the valve stopper and wherein the limited axial movement of the internal sleeve with respect to the internal body comprises sufficient movement of the internal sleeve to separate the valve stopper from the sealing surface.

21. The discharge head of claim 17, wherein the internal body is hollow.

22. The discharge head of claim 17, wherein the outlet channel comprises an outlet channel defined by the fitment of the internal body within the internal sleeve.

23. The discharge head of claim 17, wherein the spring mechanism comprises a compression spring.

24. The discharge head of claim 17, further comprising:
a fluid reservoir; and
a pump in communication with the fluid reservoir and the outlet channel.

25. A fluid dispenser, comprising:
a discharge nozzle;
a discharge opening in an end of the discharge nozzle;
a nozzle insert in the discharge opening;
an internal sleeve positioned within the discharge nozzle, wherein the internal sleeve further comprises a sealing surface adjacent to the discharge opening, an inner bush, a spring seat, an attachment element, and a snap connection holding the internal sleeve within the discharge nozzle;
an internal body positioned within the internal sleeve, wherein the internal body further comprises a valve stopper opening in an end adjacent to the discharge opening, a connecting element in an end opposite the valve stopper opening and in communication with the attachment element of the internal sleeve and allowing axial movement of the internal sleeve with respect to the internal body;
a valve stopper positioned in the valve stopper opening of the internal body;
an outlet channel defined by the location of the internal body in the internal sleeve and by the inner bush in relation to the valve stopper;
a compression spring arranged between the internal body and the internal sleeve adjacent to the valve stopper opening;
a fluid reservoir; and
a fluid discharging apparatus in communication with the fluid reservoir and connected to the connecting element of the internal body.

26. The fluid dispenser of claim 25, further comprising a medicine in the fluid reservoir.

27. The fluid dispenser of claim 25, further comprising:
depressions in the connecting element; and
protruding guide elements in the internal sleeve configured to engage the depressions in the connecting element, wherein the engagement of the depressions with the protruding guide elements may limit the axial movement of the internal sleeve with respect to the internal body.

28. The fluid dispenser of claim 25, further comprising a guide web device between the attachment element of the internal sleeve and the connecting element of the internal body.

29. The fluid dispenser of claim 25, wherein the compression spring further comprises a compression spring formed integrally with the internal body.

30. The fluid dispenser of claim 25, wherein the compression spring further comprises an annular disk.

31. The fluid dispenser of claim 25, wherein the valve stopper further comprises at least one swirling device.

32. The fluid dispenser of claim 25, wherein the valve stopper is an integral part of the internal body.

33. The fluid dispenser of claim 25, wherein the fluid discharging apparatus comprises a pump.

* * * * *